United States Patent
Ito et al.

(10) Patent No.: US 8,531,184 B2
(45) Date of Patent: Sep. 10, 2013

(54) MAGNETIC RESONANCE IMAGING APPARATUS

(75) Inventors: Kosuke Ito, Tokyo (JP); Takayuki Abe, Tokyo (JP); Masayoshi Dohata, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 358 days.

(21) Appl. No.: 13/122,593

(22) PCT Filed: Oct. 8, 2009

(86) PCT No.: PCT/JP2009/067539
§ 371 (c)(1),
(2), (4) Date: Apr. 5, 2011

(87) PCT Pub. No.: WO2010/041706
PCT Pub. Date: Apr. 15, 2010

(65) Prior Publication Data
US 2011/0181287 A1 Jul. 28, 2011

(30) Foreign Application Priority Data
Oct. 8, 2008 (JP) ................................. 2008-261474

(51) Int. Cl.
*G01V 3/00* (2006.01)
(52) U.S. Cl.
USPC .......................................... 324/307; 324/309

(58) Field of Classification Search
USPC .......................... 324/300–322; 600/407–445
See application file for complete search history.

(56) References Cited

U.S. PATENT DOCUMENTS
6,086,535 A * 7/2000 Ishibashi et al. .............. 600/439
6,963,199 B2 * 11/2005 Sato ............................... 324/306

FOREIGN PATENT DOCUMENTS
JP          5-317287       12/1993
JP         11-253416        9/1999
JP       2006-095278        4/2006

* cited by examiner

*Primary Examiner* — Brij Shrivastav
(74) *Attorney, Agent, or Firm* — Brundidge & Stanger, P.C.

(57) ABSTRACT

A magnetic resonance imaging apparatus comprises: static magnetic field generation means which generates a static magnetic field in an imaging space where an object to be examined is placed; gradient magnetic field generation means which generates a gradient magnetic field in the imaging space; high-frequency magnetic field generation means which generates a high-frequency magnetic field in the imaging space; calculation means which calculates an amount of the electromagnetic wave absorbed by the object when the high-frequency magnetic field is irradiated to the object; and a measurement means which measures a characteristic of the high-frequency magnetic field generation means.
The calculation means calculates the amount of the electromagnetic wave absorbed by the object according to the characteristic of the high-frequency magnetic field generation means measured by the measurement means.

8 Claims, 9 Drawing Sheets

FIG.7: MEASURE Q-VALUE OF RF COIL (71) → PLACE OBJECT INSIDE OF RF COIL (72) → MEASURE Q-VALUE OF RF COIL (73) → CALCULATE VOLUME OF OBJECT IN RF COIL USING VARIATION OF Q-VALUE (74) → CALCULATE BODY MASS OF OBJECT IN RF COIL (75) → INPUT IMAGING PARAMETERS (76) → CALCULATE ENERGY OF IRRADIATING RF PULSE (77) → CALCULATE PARTIAL-BODY SAR (78)

MAGNETIC RESONANCE IMAGING APPARATUS

FIELD OF THE INVENTION

The present invention relates to a magnetic resonance imaging (hereinafter referred to as MRI) apparatus, in particular to the magnetic resonance imaging apparatus capable of accurately estimating a body SAR which is one of the indices representing absorption of electromagnetic waves irradiated to an object to be examined in an imaging examination.

DESCRIPTION OF RELATED ART

An MRI apparatus comprises a static magnetic field generation device configured to generate a homogeneous static magnetic field in an imaging space, a gradient magnetic field coil configured to generate a gradient magnetic field in the imaging space, and an RF coil configured to generate a high-frequency magnetic field (RF pulse) in the imaging space, having a function to apply an RF pulse from a high-frequency coil to a target region of an object to be examined placed in a homogeneous static magnetic field space, detect a nuclear magnetic resonance (hereinafter referred to as NMR) signal produced from an imaging target region, and obtain an image effective for medical diagnosis by imaging the detected signals. The gradient magnetic field coil applies the gradient magnetic field wherein its magnetic field intensity is changed in orthogonal 3-axes directions in order to append positional information to an NMR signal.

One of the safety issues to be considered as clinically using an MRI apparatus is the energy of electromagnetic waves absorbed by an object. In accordance with the $2^{nd}$ edition of IEC 60601-2-33, the absorption amount of an RF pulse per unit time and unit mass is defined as the following arithmetic expressions as an SAR (Specific Absorption Rate), and irradiation of RF pulses is restricted so that absorption of electromagnetic waves by the human body will not exceed the upper limit value of the SAR.

$$\text{WHOLE-BODY } SAR[\text{W/kg}] = \frac{W[W]}{M[\text{kg}]} \quad (1)$$

$$\text{PARTIAL-BODY } SAR[\text{W/kg}] = \frac{W[W]}{M_P[\text{kg}]} \quad (2)$$

$$\text{LOCAL } SAR[\text{W/kg}] = \text{ENERGY TO BE ABSORBED BY ANY 10 g PER UNIT TIME} \quad (3)$$

Here, the whole-body SAR refers to the rate that the energy of electromagnetic waves absorbed by the whole-body of an object is divided by mass of the object, the partial-body SAR refers to the rate that the energy of electromagnetic waves absorbed by a desired region of the object divided by the mass of the desired region in the object and the local SAR refers to the energy of electromagnetic waves per unit time absorbed per any 10 g.

In Patent Document 1, the technique for more accurate acquisition of an SAR by detecting the RF pulse irradiated from an RF coil in real time and integrating the detected RF pulse using an integrator is disclosed.

PRIOR ART DOCUMENT

Patent Document 1: JP-A-1993-317287

However, from among the SARs that are indices representing absorption of electromagnetic energy, the partial-body SAR in particular is dependent on how much each region of an object is included inside of an RF coil in each imaging. While the conventional technique disclosed in Patent Document 1 obtains the whole-body SAR, and the method for accurately calculating the partial-body SAR dependent on the body mass of an object placed in a high-frequency pulse irradiating area by an RF coil is not disclosed therein.

The objective of the present invention is to provide an MRI apparatus capable of accurately calculating a partial-body SAR by accurately estimating the mass of an imaging target region each time that imaging target region is actually placed in a high-frequency pulse irradiating area.

BRIEF SUMMARY OF THE INVENTION

In order to achieve the above-mentioned objective, the present invention, at the time of calculating the amount of electromagnetic waves absorbed by the object upon irradiation of the high-frequency magnetic field, calculates the absorption amount of electromagnetic waves using the characteristic of the high-frequency magnetic field generation means measured by the measurement means.

EFFECT OF THE INVENTION

In accordance with the present invention, it is possible to provide an MRI apparatus capable of accurately calculating a partial-body SAR by accurately estimating the mass of an imaging target region each time that the target region is actually placed in a high-frequency pulse irradiating area.

DETAILED DESCRIPTION OF THE INVENTION

Figure 1:
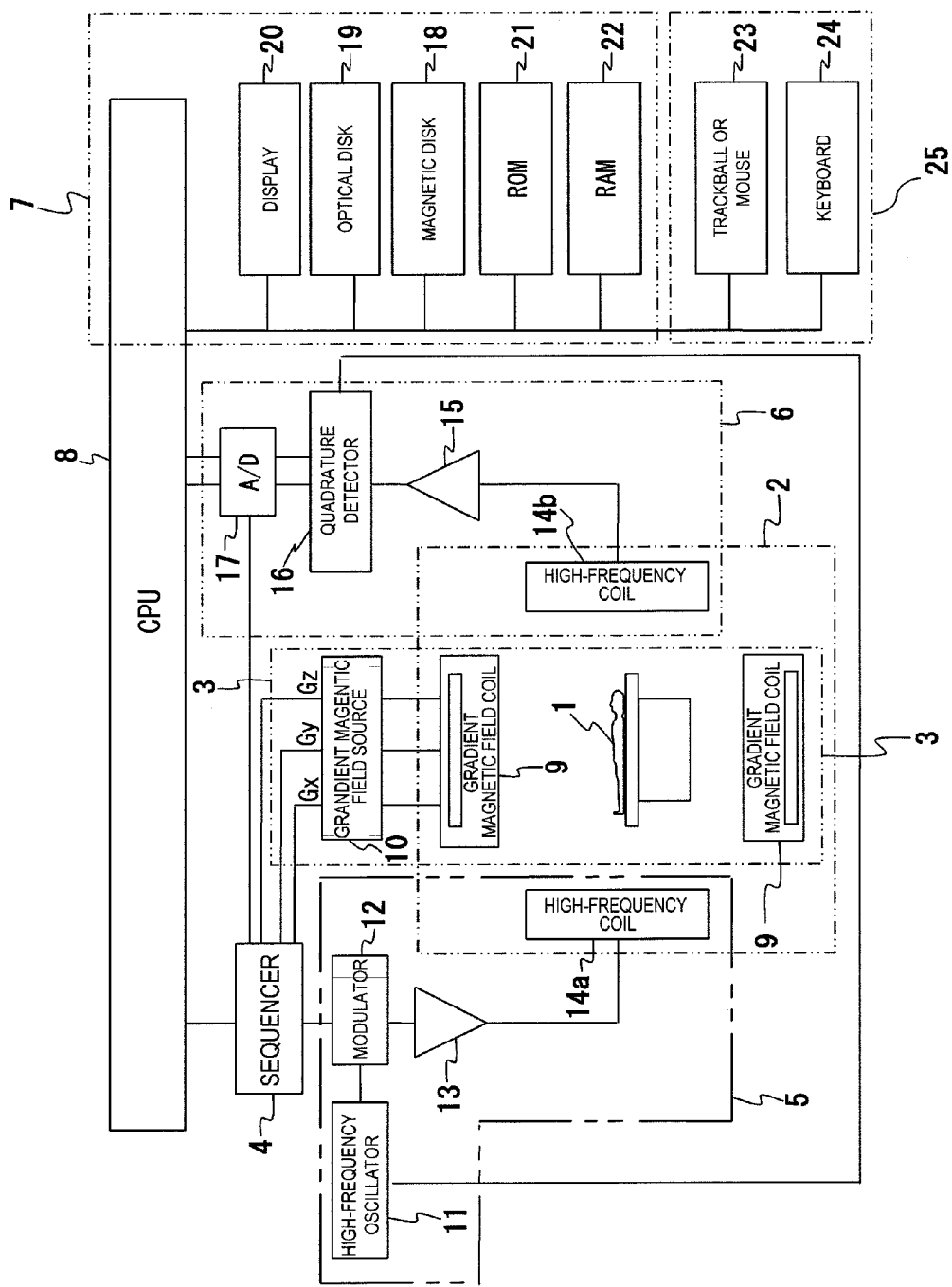
FIG. 1 is a general overview of an example of the MRI apparatus related to the present invention.

The preferable embodiments of the MRI apparatus related to the present invention will be described in detail below referring to the attached diagrams. In all diagrams for explaining embodiments of the invention, the same function parts are represented by the same reference numerals, and the duplicative description thereof is omitted.

First, the general overview of an example of the MRI apparatus related to the present invention will be described based on FIG. 1.

FIG. 1 is a block diagram showing the general configuration of an embodiment in the MRI apparatus related to the present invention. The MRI apparatus is for obtaining a tomographic image of an object to be examined using NMR phenomenon, and comprises static magnetic field generation system 2, gradient magnetic field generation system 3, transmission system 5, reception system 6, signal processing system 7, sequencer 4 and central processing unit (CPU) 8 as shown in FIG. 1.

Static magnetic field generation system 2 is for generating homogeneous static magnetic field in the direction orthogonal to the body axis in the space around object 1 when the vertical magnetic field method is used and in the body-axis direction when the horizontal magnetic field method is used, and the static magnetic field source of the permanent magnetic method, normal conducting method or superconducting method is placed around object 1.

Gradient magnetic field generation system 3 is formed by gradient magnetic field coil 9 for applying a gradient magnetic field in 3-axis direction of X, Y and Z which is the coordinate system (coordinate system at rest) of the MRI apparatus and gradient magnetic field source 10 for driving the respective gradient magnetic field coils, and applies gradient magnetic fields Gx, Gy and Gz in 3-axis directions of X, Y and Z by driving gradient magnetic field source 10 of the respective coils according to the command from sequencer 4 to be hereinafter described. At the time of imaging, gradient magnetic field generation system 3 sets the slice plane with respect to object 1 by applying slice-direction gradient magnetic field pulse (Gs) in the direction orthogonal to the slice plane (imaging cross-section), applies phase-encode direction gradient magnetic field pulse (Gp) and frequency-encode direction gradient magnetic field pulse (Gf) in the remaining two directions orthogonal to the slice plane and also to each other, and encodes the positional information to the echo signal in the respective directions.

Sequencer 4 is control means to repeatedly apply a high-frequency magnetic field pulse (hereinafter referred to as "RF pulse") and a gradient magnetic field pulse at a predetermined pulse sequence, which operates under control of CPU 8 and transmits various commands necessary for data collection of a tomographic image of object 1 to transmission system 5, gradient magnetic field generation system 3 and reception system 6.

Transmission system 5 is for irradiating an RF pulse to object 1 for causing atomic spin of an atomic element to produce nuclear magnetic resonance that form biological tissues of object 1, and is formed by high-frequency oscillator 11, modulator 12, high-frequency amplifier 13 and high-frequency coil (transmission coil) 14a. An RF pulse is irradiated to object 1 when the high-frequency pulse outputted from high-frequency oscillator 11 is amplitude-modulated by modulator 12 at the timing commanded by sequencer 4 and the amplitude-modulated high-frequency pulse is provided to high-frequency coil 14a placed in the vicinity of object 1 after being amplified by high-frequency amplifier 13.

Reception system 6 is for detecting an echo signal (NMR signal) eradiated by nuclear magnetic resonance of atomic spin forming the biological tissues of object 1, and is formed by high-frequency coil 14b on the reception side (reception coil), signal amplifier 15, quadrature detector 16 and A/D converter 17. The responsive NMR signal of object 1 excited by the electromagnetic wave irradiated from high-frequency coil 14a on the transmission side is detected by high-frequency coil 14b placed in the vicinity of object 1, amplified by signal amplifier 15, divided into diphyletic signals that are orthogonal to each other by quadrature detector 16 at the timing by the command from sequencer 4, converted into digital quantity by A/D converter 17 respectively, and transmitted to signal processing system 7.

Signal processing system 7 is for executing a variety of data processing, displaying and storing the processing results, comprising an exterior storage devices such as optical disk 19 or magnetic disk 18 and display 20 formed by CRT, etc. When the data from reception system 6 is inputted to CPU 8, CPU 8 executes processing such as signal processing and image reconstruction, displays the tomographic image of object 1 which is the result of the processing on display 20, and stores the image in magnetic disk 18, etc. of the external storage device.

Operation unit 25 is for inputting a variety of control information of an MRI apparatus or control information of the processing to be executed in the above-mentioned signal processing unit 7, and is formed by a trackball or mouse 23 and keyboard 24. Operation 25 is to be placed in the vicinity of display 20. The operator controls a variety of processing of the MRI apparatus interactively via operation unit 25 while observing display 20.

In FIG. 1, high-frequency coil 14a on the transmission side and gradient magnetic field coil 9 are placed facing object 1 when the vertical magnetic field method is used and surrounding object 1 when the horizontal magnetic field is used, in a static magnetic field space of static magnetic field generation system 2 in which object 1 is inserted. Also, high-frequency coil 14b on the reception side is placed facing object 1 or surrounding object 1.

Currently the kind of imaging object nucleus which is clinically pervading is hydrogen nucleus (proton) which is the main constituent of an object. By imaging the information related to the spatial distribution of proton density or spatial distribution of relaxation time in the excited condition, 2-dimensional or 3-dimensional imaging of configuration or function of a head portion, abdominal portion, extremities, etc. of a human body is executed.

Embodiment 1

Next, embodiment 1 of the present invention will be described. Embodiment 1 of the present invention uses the characteristic of the RF coil which is dependent on the volume of an imaging region of the object included in the RF coil. More specifically, by measuring the characteristic of the RF coil, the volume of the imaging region of the object placed in the RF coil is obtained in the condition that the object is placed inside of the RF coil. Further, the body mass of the imaging region of the object placed in the RF coil is calculated by multiplying the obtained volume of the imaging region by the density, and the partial-body SAR in the condition that the object is placed in the RF coil is calculated using the body mass. First, the concept of embodiment 1 related to the present invention will be described.

The impedance of the RF coil can be expressed as arithmetic expression (4) below since it is dependent on the volume of the irradiation space inside of the RF coil.

$$Z = f(v) \quad (4)$$

Here, Z represents the impedance of the RF coil, and V represents the volume of the irradiation space in the RE coil respectively.

Therefore, measuring the impedance and obtaining function f thereof with respect to the RF coil having a variety of volumes, the volume of the irradiation space in the RF coil can be calculated as arithmetic expression (5).

$$V=f^{-1}(Z) \qquad (5)$$

Further, the impedance in the condition that the object is placed in the RF coil can be obtained by arithmetic expression (6).

$$Z'=f(V-V_1)+g(V_1) \qquad (6)$$

Here, $V_1$ represents the volume of the object in the RF coil, and the impedance in the condition that the object is placed in the RF coil is assumed to be obtained by arithmetic expression (6) as the sum of the term that depends on the volume of the part in the RF coil where the object is not placed and the term that depends on the volume of the part in the RF coil where the object is placed.

Therefore, by empirically obtaining function h while simply expressing arithmetic expression (6) as $Z'=h(V_1)$, the volume of the object placed in the RF coil can be calculated by measuring the impedance in the condition that the object is actually placed.

By multiplying the obtained volume of the object in the RF coil by density $\rho$ of the object (for example, $\rho$ can be set as 1 g/cm³ by approximating by the density of water), mass Mp of the part where the RF pulse is irradiated can be obtained as arithmetic expression (7).

$$Mp=\rho \times V_1 \qquad (7)$$

From the obtained partial mass and energy W[W] of the RF pulse to be absorbed, partial-body SAR can be calculated by arithmetic expression (8).

$$\text{PARTIAL-BODY } SAR[\text{W/kg}] = \frac{W[W]}{M_p[\text{kg}]} \qquad (8)$$

Energy W[W] of the RF pulse to be absorbed is calculated using the ratio of the reference RF pulse in which the energy to be absorbed is measured in advance to the RF pulse to be actually used, concretely by arithmetic expression (9).

$$W[W] = Wc \times \frac{T_0}{T} \times \frac{S}{S_0} \times \left(\frac{FA}{FA_0}\right)^2 \qquad (9)$$

Here, Wc represents the absorption amount of the RF pulse measured using the reference RF pulse, $T_0$ represents the application time of the reference RF pulse, $S_0$ represents the amount wherein the square of the function that the waveform of the reference RF pulse is normalized to [0:1] is integrated from time t=0 to t=$T_0$, and $FA_0$ represents the flip angle of the reference pulse. Also, T represents the application time of the RF pulse to be actually used, S represents the square of the function wherein the waveform of the RF pulse to be actually used is normalized to [0:1] is integrated from time t=0 to time t=T, and FA represents the flip angle of the RF pulse to be actually used respectively. In this regard, however the measurement of Wc is executed by irradiating the reference pulse reference pulse, measuring the energy of the incident wave and the reflected wave, and calculating the difference of the measured energies for measuring the power of the absorbed RF pulse.

Figure 2:
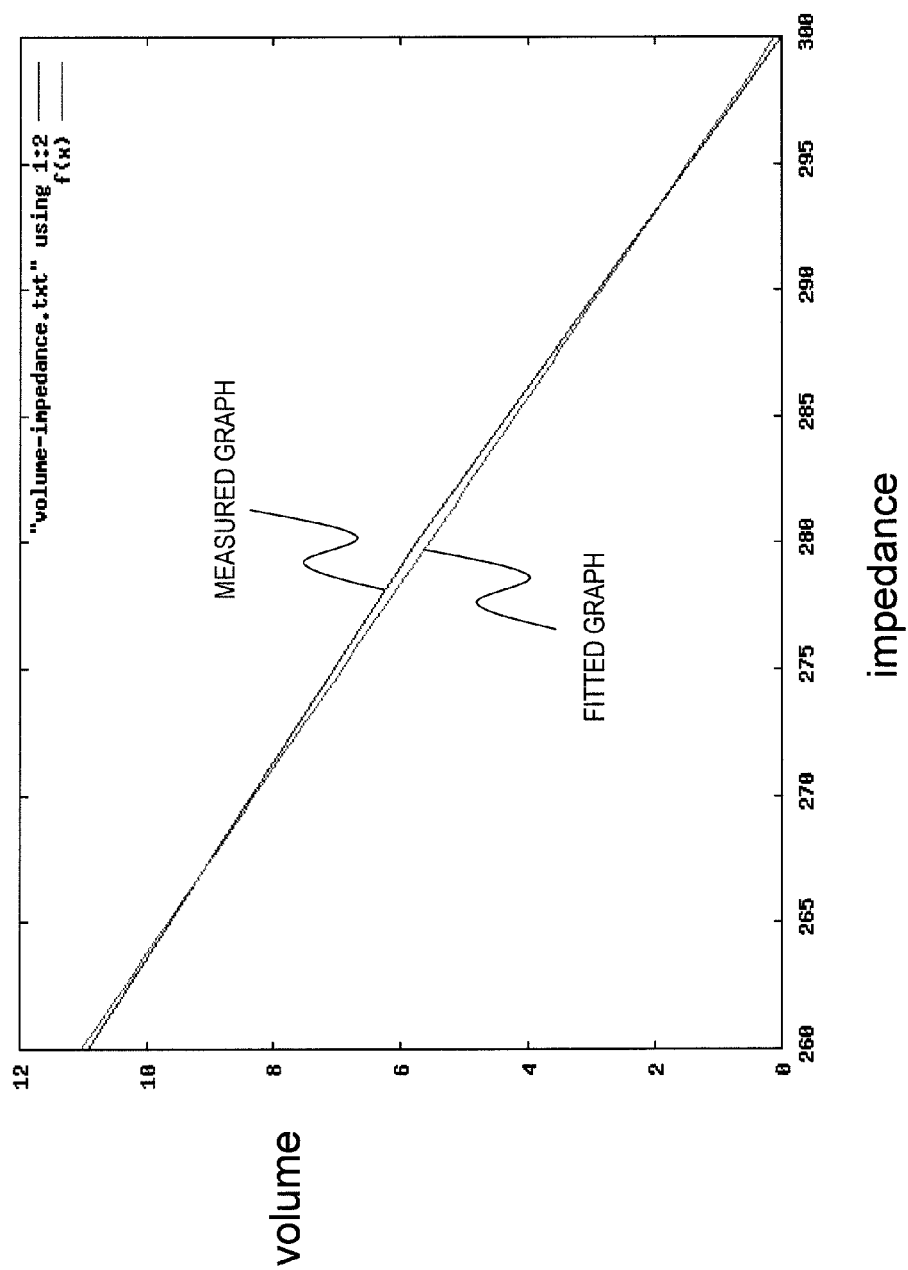
FIG. 2 is a graph showing the relationship between the impedance actually measured using a phantom and the volume.

FIG. 2 is a graph showing the relationship between the impedance actually measured using a phantom and the volume. When the measured volume and the impedance are fitted using a given function by the least-square method, the error was 3%. In embodiment 1 of the present invention, as shown in FIG. 2, function h is empirically obtained and the volume of the object placed in the RF coil is calculated.

Figure 3:
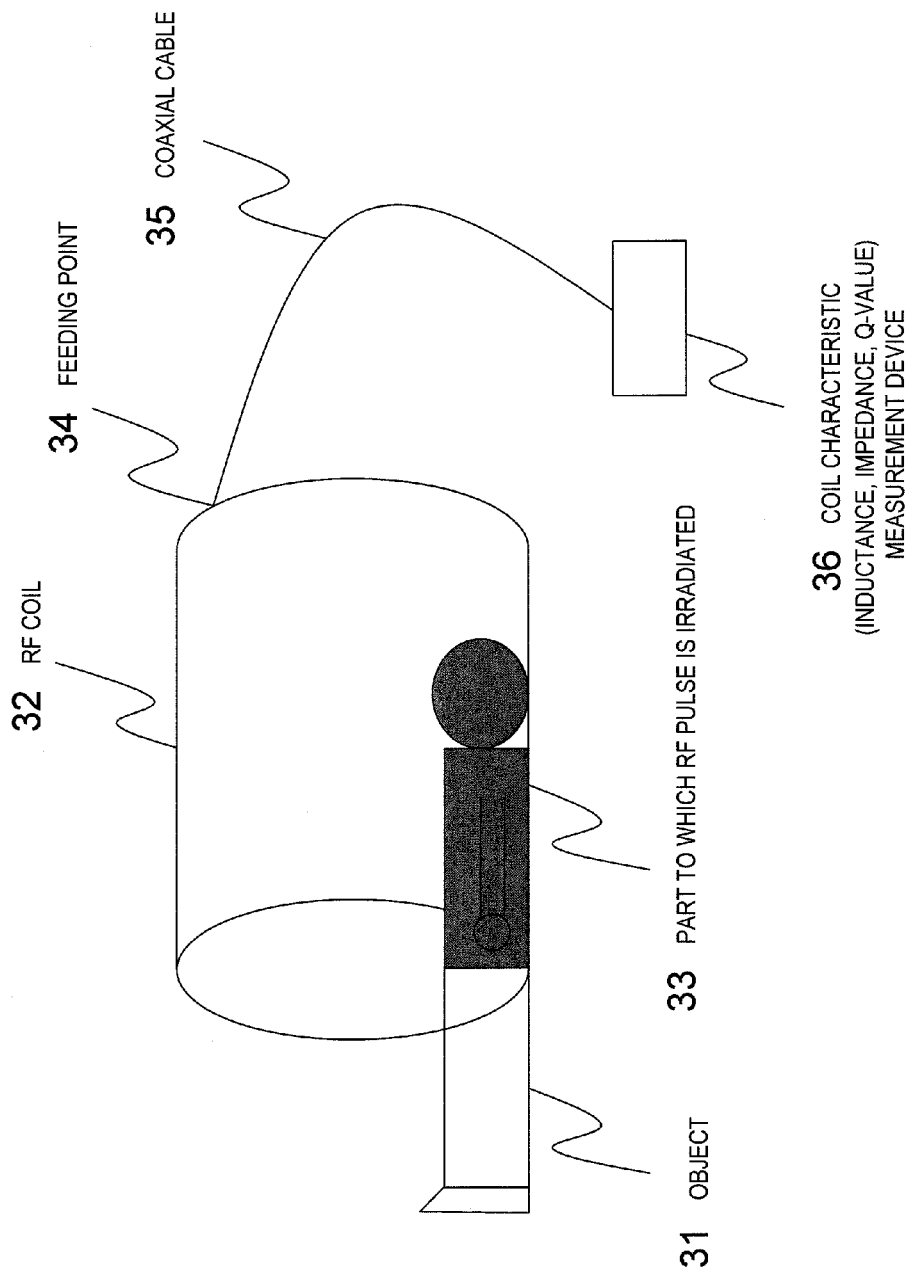
FIG. 3 is a pattern diagram showing measurement of the volume of an object which is actually housed inside of an RF coil.

FIG. 3 shows a pattern diagram of the time of measuring the volume of the object when it is actually placed in the RF coil. In FIG. 3, an object is indicated by 31, an RF coil is indicated by 32 and the part to which an RF pulse is irradiated in the object is indicated by 33. The RF coil has feeding point 34 that provides electricity, which is connected to coil characteristic measuring device 36 by coaxial cable 35. Here, coil characteristic measuring device 36 is set as capable of measuring the impedance of the RF coil.

Figure 4:
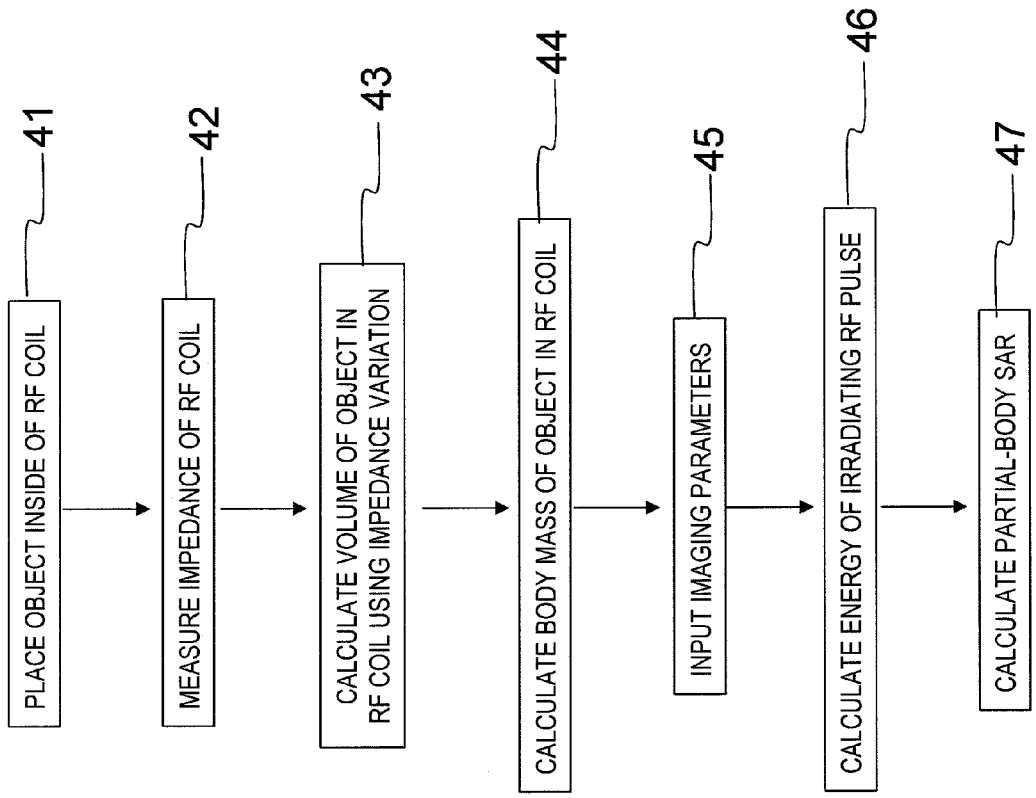
FIG. 4 is a flowchart showing the operation of embodiment 1.

Next, the operation of embodiment 1 will be described using the flowchart in FIG. 4.

(Step 41)
An object is placed inside of an RF coil.
(Step 42)
The impedance of the RF coil is measured.
(Step 43)
The volume of the object (gray part in FIG. 3) placed in the RF coil is calculated in accordance with the graph in FIG. 2.
(Step 44)
The mass of the object in the RF coil is calculated based on arithmetic expression (7) from the volume obtained in step 43.
(Step 45)
The imaging parameters are inputted.
(Step 46)
Energy of the RF pulse irradiated to the object is calculated.
(Step 47)
The partial-SAR is obtained by calculating in accordance with arithmetic expression (8) using the energy and the mass obtained in step 44, and compared with the limit value.

In accordance with the above-described embodiment, it is possible to accurately estimate the partial-body SAR from among the indices representing the energy absorption of the electromagnetic waves irradiated to the object using the simple method. In concrete terms, the MRI apparatus related to the present invention comprising calculation means configured to calculate the amount of the electromagnetic waves absorbed by the object upon irradiation of a high-frequency magnetic field to the object is provided with measurement means configured to measure the characteristic of the high-frequency magnetic field generation means, and the measurement means is characterized in calculating the absorption amount of electromagnetic waves to the object based on the characteristic of the high-frequency magnetic field generation means. More concretely, the absorption amount of electromagnetic waves to the object is obtained using the volume of the part of the object to which the high-frequency magnetic field is irradiated.

In other words, since the volume of the part of the object to be placed in the RF coil can be accurately estimated using the graph (function) obtained in advance by measuring the characteristic of the coil by the coil characteristic measuring device, the mass of the part to which the high-frequency pulse is actually irradiated can be accurately obtained by multiplying the obtained volume by the density of the object. Further, the partial-body SAR depending on the mass can be accurately estimated. When the partial-body SAR can be accurately obtained, determination on whether the imaging sequence should be actually executed or not can be accurately carried out.

Embodiment 2

Next, embodiment 2 of the present invention will be described. The difference from embodiment 1 is that the partial-body SAR is calculated using the inductance of an RF coil. Also, the case of using a solenoid coil as the RF coil is assumed in embodiment 2. In the following description, only the function parts that are different from embodiment 1 will be described and the same function parts will be omitted. First, the concept of the present embodiment will be described below.

The inductance of the solenoid coil is expressed by arithmetic expression (10).

$$L_0 = \mu_0 n^2 V_0 \qquad (10)$$

Here, $L_0$ represents the inductance of an air-core coil, $\mu_0$ represents magnetic permeability of air, n represents the winding number per unit length of the coil, and $V_0$ represents the volume of the coil respectively. The inductance of the condition that the object is placed inside of the coil can be expressed by arithmetic expression (11).

$$L' = \mu_1 n^2 V_1 + \mu_0 n^2 (V_0 - V_1) \qquad (11)$$

Here, L' represents the inductance at the time that the object is placed inside of the coil, $\mu_1$ represents magnetic permeability of the object, and $V_1$ represents the volume of the object in the coil respectively. By using arithmetic expression (11), the volume of the object in the coil can be obtained by arithmetic expression (12).

$$V_1 = \frac{L' - L_0}{n^2(\mu_1 - \mu_0)} \qquad (12)$$

By multiplying the obtained volume of the object in the coil by density ρ of the object, mass Mρ of the part to which the RF pulse is irradiated can be obtained as arithmetic expression (13).

$$M\rho = \rho \times V_1 \qquad (13)$$

The partial-body SAR can be calculated using arithmetic expression (14) from the obtained partial mass and energy W[W] of the absorbed RF pulse.

$$\text{PARTIAL-BODY } SAR[\text{W/kg}] = \frac{W[W]}{M_p[\text{kg}]} \qquad (14)$$

The W[W] can be calculated as in embodiment 1 using the ratio of the reference RF pulse of which the energy to be absorbed is measured in advance to the RF pulse to be actually used.

Figure 5:
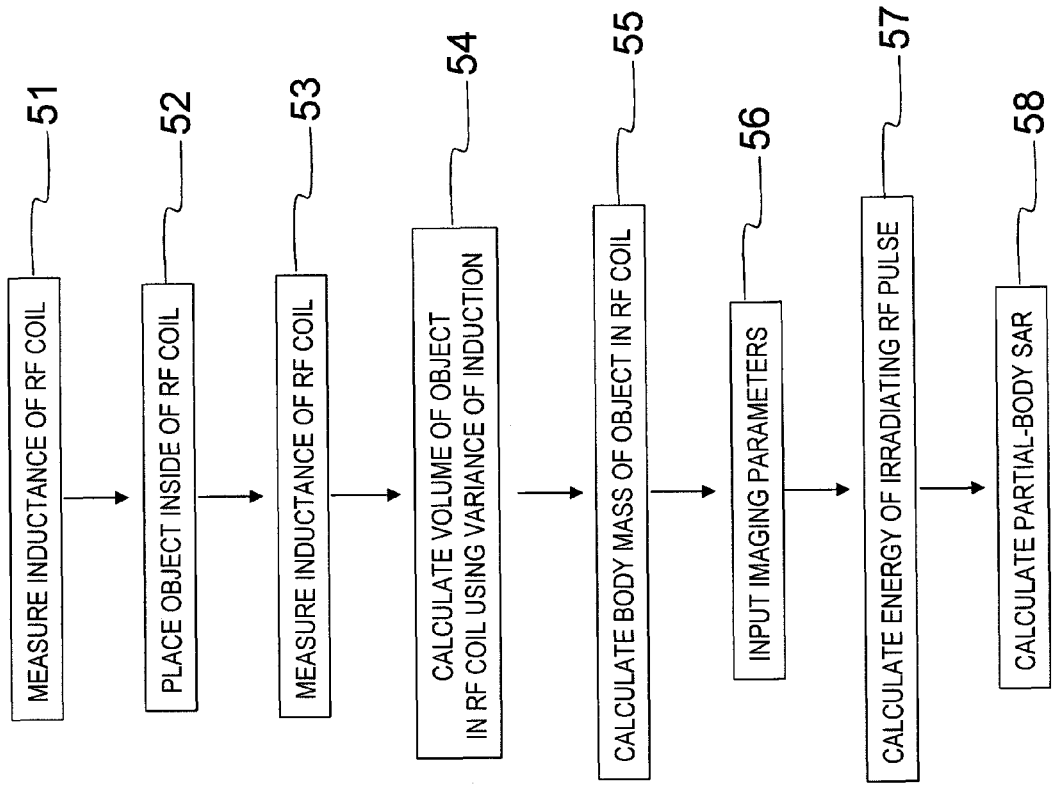
FIG. 5 is a flowchart showing the operation of embodiment 2.

Next, the operation in embodiment 2 will be described using the flowchart in FIG. 5.

(Step 51)

First, the inductance of the RF coil (FIG. 2) is measured in the condition that an object is not placed in the RF coil.

(Step 52)

The object is placed inside of the RF coil.

(Step 53)

The inductance of the RF coil is measured again.

(Step 54)

The volume of the object in the RF coil (the gray part in FIG. 3) is calculated according to arithmetic expression (12).

(Step 55)

The mass of the object in the RF coil is calculated according to arithmetic expression (13) from the obtained volume.

(Step 56)

The imaging parameters are inputted.

(Step 57)

The energy of the RF pulse to be irradiated to the object is calculated.

(Step 58)

The partial-body SAR is calculated according to arithmetic expression (14) using the energy and the partial mass, and is compared to the partial-body SAR limit value.

In accordance with the present embodiment, it is possible to accurately calculate a partial-body SAR without pre-measurement for acquiring the graph shown in FIG. 2 as in embodiment 1, since the partial-body SAR is obtained using the variation of the inductance using the electromagnetic formulas assuming that the pattern of the RF coil is a solenoid coil.

Embodiment 3

Next, embodiment 3 will be described. The difference from embodiment 2 is that the impedance, not the inductance is used for calculation of a partial-body SAR. Also, the case for using a solenoid coil is used as an RF coil is assumed. In the following description, only the different function parts are described, and the duplicative description of the same function parts is omitted. First, the concept of the present embodiment will be described.

The present embodiment is the method to measure the impedance when an object is placed inside of an RF coil of an MRI apparatus. The volume of the object is to be calculated from the variation of the obtained impedance.

More concretely, the relationship expressed in arithmetic expression (15) exists between the impedance and the inductance.

$$Z = R + i\omega L \qquad (15)$$

Here, Z represents the impedance of a coil, R represents resistance, ω represents frequency and i represents imaginary unit. By using arithmetic expression (12) and arithmetic expression (15), the relationship between the impedance and the volume of the object in the RF coil can be obtained as arithmetic expression (16).

$$V_1 = \frac{1}{n^2(\mu_1 - \mu_0)} \text{Im}\left(\frac{Z'}{\omega'} - \frac{Z_0}{\omega_0}\right) \qquad (16)$$

Therefore, the volume of the object in the RF coil can be calculated by measuring the variation of the impedance upon placing the object inside of the RF coil.

Figure 6:
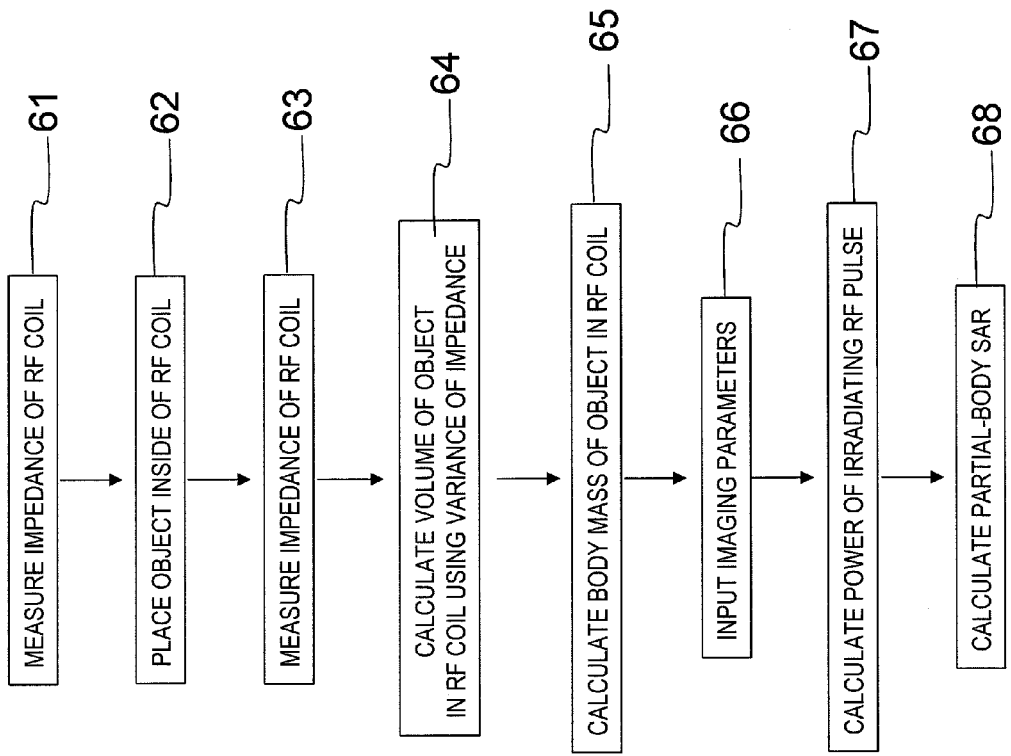
FIG. 6 is a flowchart showing the operation of embodiment 3.

Next, the operation of embodiment 3 will be described using the flowchart in FIG. 6.

(Step 61)

First, the impedance of the RF coil is measured in the condition that the object is not placed.

(Step 62)

The object is placed inside of the RF coil.

(Step 63)

The impedance of the RF coil is measured again.

(Step 64)

The volume of the object in the RF coil (the gray part in FIG. 2) is calculated according to arithmetic expression (16).

(Step 65)
The mass of the object in the RF coil is calculated from the obtained volume according to arithmetic expression (16).
(Step 66)
The imaging parameters are inputted.
(Step 67)
The energy of the RF pulse to be irradiated to the object is calculated.
(Step 68)
The partial-body SAR is calculated using the energy and the partial mass according to arithmetic expression (8), and is compared to the partial-body SAR limit value.

In accordance with the present embodiment, it is possible to accurately obtain a partial-body SAR without pre-measurement for acquiring the graph in FIG. 2 as in embodiment 1, since the partial-body SAR is obtained using the variance of the impedance using the electromagnetic formulas assuming that the pattern of the RF coil is a solenoid coil.

Embodiment 4

Next, embodiment 4 will be described. The difference from embodiments 1~3 is that the Q-value of an RF coil, not the impedance or inductance is used for calculation of a partial-body SAR. Also, the case for using the solenoid coil as an RF coil is assumed. In the following description, the only different function parts are described, and the duplicative description of the same function parts is omitted. First, the concept of the present embodiment will be described.

The present embodiment is the method to measure the Q-value before and after the object is placed inside of the RF coil of an MRI apparatus. The volume of the object is calculated from the variation of the obtained Q-value.

More concretely, the Q-value of the coil is acquired by arithmetic expression (17).

$$Q = \frac{\omega L}{R} \quad (17)$$

By using the arithmetic expression (12) and arithmetic expression (17), the relationship between the Q-value and the volume of the object in the RF coil can be expressed as arithmetic expression (18).

$$V_1 = \frac{1}{n^2(\mu_1 - \mu_0)} \left[ \frac{R_1 Q_1}{\varpi_1} - \frac{R_0 Q_0}{\varpi_0} \right] \quad (18)$$

Therefore, the volume of the object in the RF coil can be obtained by measuring the variation of the Q-value when the object is inserted inside of the RF coil.

Figure 7:
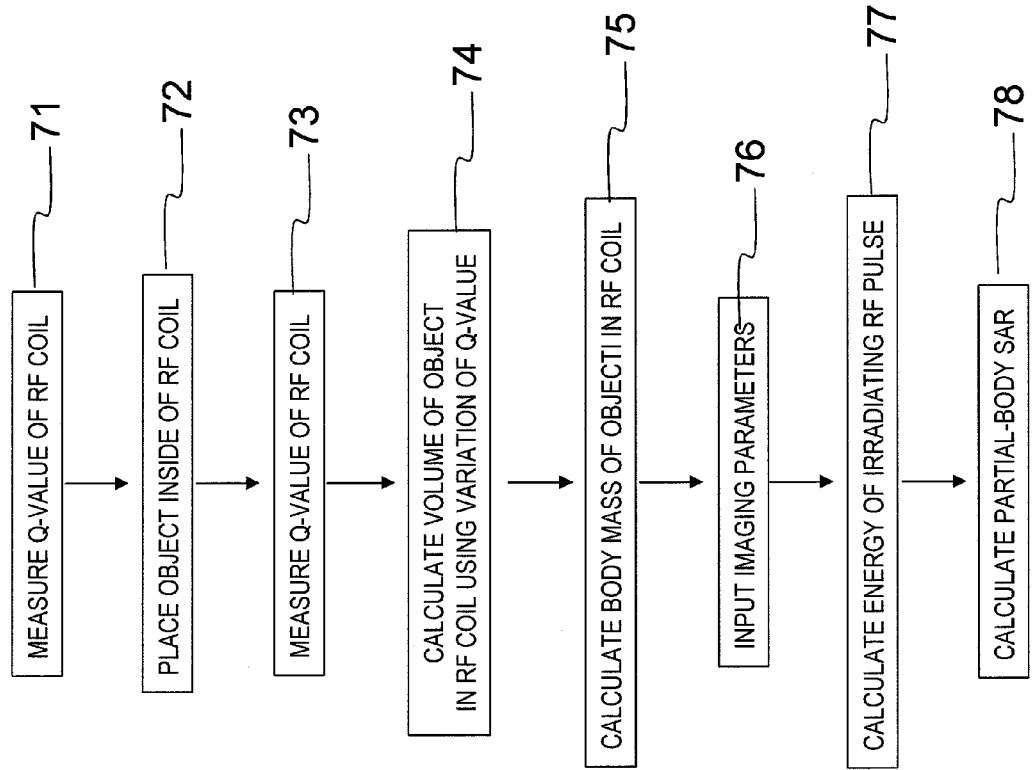
FIG. 7 is a flowchart showing the operation of embodiment 4.

Next, the operation of embodiment 4 will be described using the flowchart in FIG. 7.
(Step 71)
First, Q-value of the RF coil is measured in the condition that the object is not placed inside of the RF coil.
(Step 72)
The object is placed inside of the RF coil.
(Step 73)
The Q-value of the RF coil is measured again.
(Step 74)
The volume of the object in the RF coil (the gray part in FIG. 2) is calculated according to arithmetic expression (18).

(Step 75)
The mass of the object in the RF coil is calculated using the obtained volume according to arithmetic expression (13).
(Step 76)
The imaging parameters are inputted.
(Step 77)
The energy of the RF pulse to be irradiated to the object is calculated.
(Step 78)
The partial SAR is calculated according to arithmetic expression (14) using the energy and the partial mass, and is compared with the partial-body SAR limit value.

In accordance with the present embodiment, it is possible to accurately obtain a partial-body SAR without pre-measurement for acquiring the graph in FIG. 2 as in embodiment 1, since the partial-body SAR is obtained using the variance of the Q-values using an electromagnetic formulas assuming that the pattern of the RF coil is a solenoid coil.

Embodiment 5

Next, embodiment 5 will be described. The difference from embodiment 1-embodiment 4 is that the partial-body SAR is calculated using density of the object that varies depending on an imaging region. In the following description, only the different function parts are described, and the duplicative description of the same function parts is omitted.

When density of an object is set as $\rho(z)[kg/cm^3]$, a partial mass can be obtained by arithmetic expression (19).

$$M_p(z) = \rho(z) \times V_1 \quad (19)$$

Here, $V_1$ is the volume of an object in the RF coil obtained by one of the methods described in embodiments 1~4.

The partial-body SAR is calculated according to arithmetic expression (8) using the partial mass calculated by arithmetic expression (19).

Figure 8:
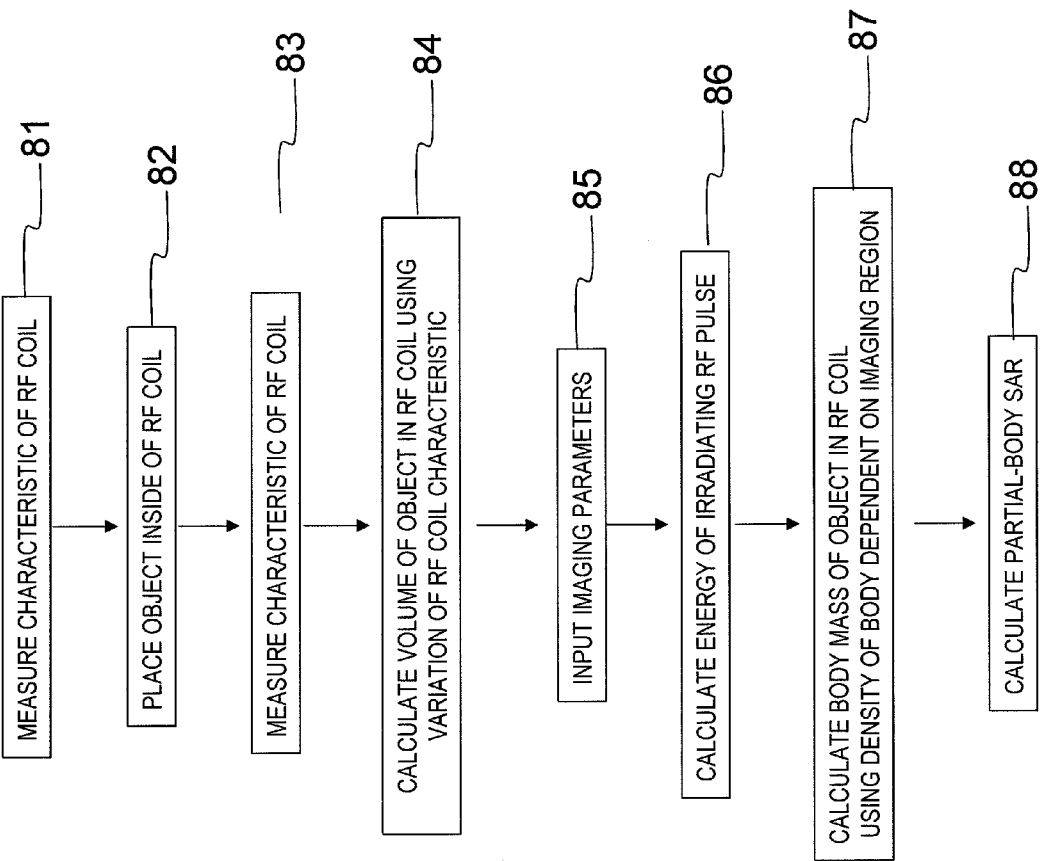
FIG. 8 is a flowchart showing the operation of embodiment 5.

Next, the operation of embodiment 6 will be described using the flowchart in FIG. 8.
(Step 81)
First, the characteristic of the RF coil (FIG. 2) is measured in the condition that the object is not placed in the RF coil.
(Step 82)
The object is placed in the RF coil.
(Step 83)
The characteristic of the RE coil is measured again.
(Step 84)
The volume of the object in the RF coil (the gray part in FIG. 2) is calculated.
(Step 85)
The imaging parameters are inputted.
(Step 86)
The energy to be irradiated to the object is calculated.
(Step 87)
The mass of the object in the RF coil is calculated according to arithmetic expression (19) using the body density for each imaging region which is measured in advance, in accordance with the imaging region inputted by the operator of the MRI apparatus.
(Step 88)
The RF energy to be absorbed by the object is calculated using the imaging parameters. The partial-body SAR is calculated according to arithmetic expression (8) from the obtained mass of the object and the RF energy to be absorbed.

In accordance with the present embodiment, it is possible to accurately calculate a partial-body SAR since the density of each imaging region of the object is accurately estimated.

Embodiment 6

Figure 9:
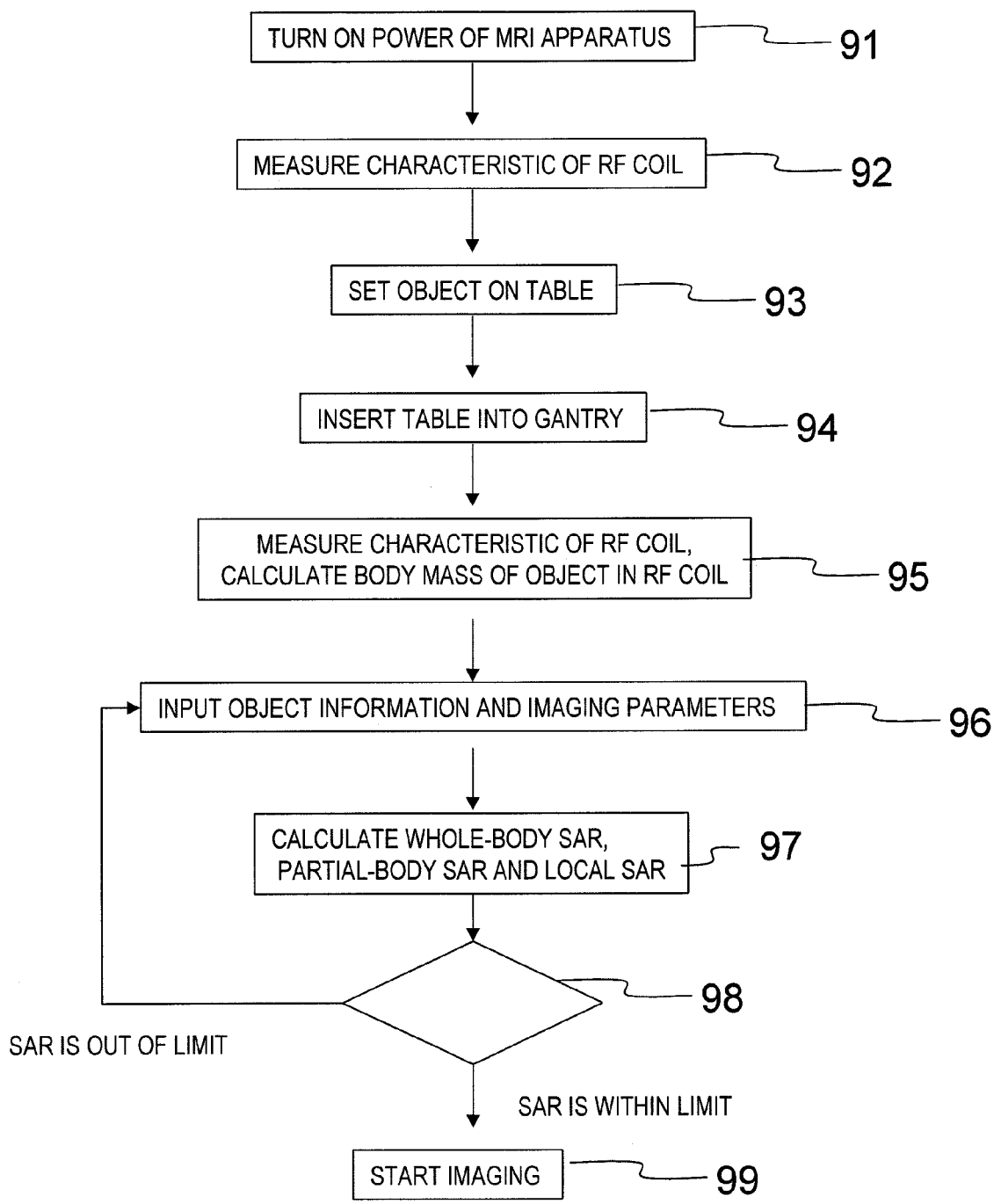
FIG. 9 shows the workflow that is common in embodiments 1~5.

The workflow which is common in the above-described embodiments 1~5 will be described using FIG. 9.

(Step 91)
First, an MRI operator turns on an MRI apparatus.

Next, the MRI apparatus measures the characteristic of an RF coil in the condition that an object is not placed inside of the RF coil. At this time, the characteristic of the RF coil measured at the time of adjustment of the MRI apparatus may also be used without executing the actual measurement.

(Step 93)
Next, the MRI operator sets the object on a table.

(Step 94)
The table is inserted in a gantry.

(Step 95)
The MRI apparatus measures the characteristic of the RF coil in the condition that the object is placed inside of the RF coil. Further, the mass of the object in the RF coil is calculated using the method described in embodiments 1~5 using the obtained characteristic of the RF coil.

(Step 96)
The MRI operator inputs object's information and imaging parameters.

(Step 97)
The MRI apparatus calculates the whole-body SAR, partial-body SAR and local SAR using the inputted imaging parameters, object's information and the calculated mass of the object in the RF coil.

(Step 98)
The MRI apparatus compares the calculated SAR with the SAR limit value, and returns to the input of imaging parameters in the case that the SAR surpasses the SAR limit value. In the case that the SAR does not surpass the SAR limit value, the MRI apparatus starts imaging.

As described in the embodiment above, the partial-body SAR which is dependent on the mass of the part to which a high-frequency pulse is actually irradiated can be accurately estimated. Further, determination on whether to actually execute imaging sequence can be accurately made using the partial-body SAR.

DESCRIPTION ON REFERENCE NUMERALS

31: object, 32: RF coil, 33: the part of an object to which an RF pulse is irradiated, 34: feeding point for providing electricity to an RF coil, 35: coaxial cable, 36: coil characteristic measuring device

The invention claimed is:

1. A magnetic resonance imaging apparatus comprising:
  static magnetic field generation means configured to generate a static magnetic field in an imaging space in which an object to be examined is placed;
  gradient magnetic field generation means configured to generate a gradient magnetic field in the imaging space;
  high-frequency magnetic field generation means configured to generate a high-frequency magnetic field in the imaging space; and
  calculation means configured to calculate the amount of electromagnetic waves absorbed by the object upon irradiation of the high-frequency magnetic field to the object,
  characterized in comprising measurement means configured to measure the characteristic of the high-frequency magnetic field generation means,
  wherein the calculation means calculate the amount of the electromagnetic waves absorbed by the object based on the characteristic of the high-frequency magnetic field generation means measured by the measurement means.

2. The magnetic resonance imaging apparatus according to claim 1, wherein the amount of electromagnetic waves absorbed by the object is obtained using the volume of the part of the object to which the high-frequency magnetic field is irradiated.

3. The magnetic resonance imaging apparatus according to claim 2, wherein the high-frequency magnetic field generation means includes an RF coil, and the volume is calculated using impedance of the RF coil as the characteristic.

4. The magnetic resonance imaging apparatus according to claim 2, wherein the high-frequency magnetic field generation means includes an RF coil, and the volume is calculated using inductance of the RF coil as the characteristic.

5. The magnetic resonance imaging apparatus according to claim 2, wherein the high-frequency magnetic field generation means includes an RF coil, and the volume is calculated using the Q-value of the RF coil as the characteristic.

6. The magnetic resonance imaging apparatus according to claim 1, wherein the amount of electromagnetic waves absorbed by the object is defined as a partial-body SAR.

7. The magnetic resonance imaging apparatus according to claim 6, wherein:
  the high-frequency magnetic field generation means is an RF coil, and
  the partial-body SAR is calculated by dividing irradiation energy of electromagnetic waves generated from the high-frequency magnetic field generation means by the mass which is the product of volume and density of the region to which a high-frequency magnetic field is irradiated in the object placed inside of the RF coil.

8. The magnetic resonance imaging apparatus according to claim 7, wherein the volume of the region in the object to which a high-frequency magnetic field is irradiated is calculated based on the characteristic of the RF coil.

* * * * *